US008241654B2

(12) United States Patent
Stopek

(10) Patent No.: US 8,241,654 B2
(45) Date of Patent: Aug. 14, 2012

(54) REACTIVE SURGICAL IMPLANT

(75) Inventor: Joshua B. Stopek, Yalesville, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 219 days.

(21) Appl. No.: 12/548,524

(22) Filed: Aug. 27, 2009

(65) Prior Publication Data
US 2010/0080838 A1 Apr. 1, 2010

Related U.S. Application Data

(60) Provisional application No. 61/100,392, filed on Sep. 26, 2008.

(51) Int. Cl.
*A61F 2/00* (2006.01)
*A01N 43/02* (2006.01)
(52) U.S. Cl. ........................ 424/423; 514/449
(58) Field of Classification Search ........................ None
See application file for complete search history.

(56) References Cited

U.S. PATENT DOCUMENTS

| | | | |
|---|---|---|---|
| 6,322,588 B1 | 11/2001 | Ogle et al. | |
| 6,391,060 B1 | 5/2002 | Ory et al. | |
| 6,408,656 B1 | 6/2002 | Ory et al. | |
| 6,443,964 B1 | 9/2002 | Ory et al. | |
| 6,451,032 B1 | 9/2002 | Ory et al. | |
| 6,478,727 B2 | 11/2002 | Scetbon | |
| 6,565,580 B1 | 5/2003 | Beretta | |
| 6,596,002 B2 | 7/2003 | Therin et al. | |
| 6,624,138 B1 | 9/2003 | Sung et al. | |
| 6,670,454 B2 | 12/2003 | Lai et al. | |
| 6,695,855 B1 | 2/2004 | Gaston | |
| 6,971,252 B2 | 12/2005 | Therin et al. | |
| 6,974,862 B2 | 12/2005 | Ringeisen et al. | |
| 7,021,086 B2 | 4/2006 | Ory et al. | |
| 7,156,804 B2 | 1/2007 | Nicolo | |
| 2002/0177223 A1 | 11/2002 | Ogle et al. | |
| 2002/0182261 A1 | 12/2002 | Dai et al. | |
| 2002/0193812 A1* | 12/2002 | Patel et al. | 606/151 |
| 2004/0078074 A1 | 4/2004 | Anderson et al. | |
| 2005/0019404 A1 | 1/2005 | Sung et al. | |
| 2005/0085817 A1 | 4/2005 | Ringeisen | |
| 2005/0123581 A1 | 6/2005 | Ringeisen et al. | |
| 2005/0123582 A1 | 6/2005 | Sung et al. | |
| 2005/0163818 A1 | 7/2005 | Sung et al. | |
| 2005/0163821 A1 | 7/2005 | Sung et al. | |
| 2005/0171616 A1 | 8/2005 | Sung et al. | |
| 2005/0283255 A1 | 12/2005 | Geremakis et al. | |
| 2006/0002980 A1 | 1/2006 | Ringeisen et al. | |
| 2006/0034885 A1 | 2/2006 | Sung et al. | |
| 2006/0085034 A1 | 4/2006 | Bettuchi | |
| 2006/0147539 A1 | 7/2006 | Sung et al. | |
| 2006/0148724 A1 | 7/2006 | Zhang et al. | |
| 2006/0149392 A1 | 7/2006 | Hsieh et al. | |
| 2006/0177480 A1 | 8/2006 | Sung et al. | |
| 2006/0193885 A1 | 8/2006 | Neethling et al. | |
| 2007/0032805 A1 | 2/2007 | Therin et al. | |
| 2007/0111937 A1* | 5/2007 | Pickar et al. | 514/12 |
| 2007/0170080 A1 | 7/2007 | Stopek et al. | |

FOREIGN PATENT DOCUMENTS

| | | |
|---|---|---|
| EP | 1 244 478 | 10/2002 |
| WO | WO 98/19718 | 5/1998 |
| WO | WO 2009/105265 A2 | 8/2009 |

OTHER PUBLICATIONS

Sung, Hsing-Wen, et al., J. Biomater. Sci. Polymer Edn. vol. 10, No. 7, pp. 751-771 (1999).*
Zhu, Yabin, et al., Denisty quantification of collagen grafted on biodegradable polyester: Its application to esophageal smooth muscle cell, Analytical biochemistry (2007), 363, pp. 119-127.*
Sung, Hsing-Wen et al., Stability of biological tissue fixed with a naturally occurring crosslinking agent (genipin), J. Biomed Mater Res (2001), 55, pp. 538-546.*
European Search Report for corresponding European Application No. EP 10251911.2 completed Mar. 11, 2011 (3 pgs).
Huang K S et al.: "Microfluidic Controlling Monodisperse Microdroplet For 5-Fluorouracil Loaded Genipin-Gelatin Microcapsules", Journal of Controlled Release, Elsevier, Amsterdam, NL, vol. 137, No. 1, Jul. 1, 2009, pp. 15-19 (XP026161192).
Ohya Y et al.: "Preparation Of Albumin Microspheres Grafted Galactose Residues Through Polyethylene-Glycol Spacers, Release Behavior Of 5-Fluorouracil From Them, And Their Lectin-Mediated Aggregation", Journal of Macromolecular Science: Part A—Chemistry, Marcel Dekker, NY, NY, vol. A28, No. 8, Jan. 1, 1991, pp. 743-760 (XP002060122).

* cited by examiner

*Primary Examiner* — Brian-Yong S Kwon
*Assistant Examiner* — Lyndsey Beckhardt

(57) ABSTRACT

Biocompatible implants including a polymer substrate and a reactive component for implant fixation in situ. The reactive component in combination with the substrate creates a reactive implant which bonds to a tissue surface in situ.

11 Claims, 2 Drawing Sheets

REACTIVE SURGICAL IMPLANT

CROSS-REFERENCE TO RELATED APPLICATIONS

This application claims the benefit of and priority to U.S. Provisional Application No. 61/100,392, filed on Sep. 26, 2008, the entire disclosure of which is incorporated by reference herein.

TECHNICAL FIELD

The present disclosure relates to a reactive implant which crosslinks to a tissue surface in situ.

BACKGROUND

The use of medical devices, and more specifically, implants, are known. However, the implants, once placed in situ, may dislocate or migrate resulting in damage to the surrounding tissue, or device failure depending on the type and location of the implant. Therefore, implants such as meshes, are frequently secured to tissue during surgery using surgical tacking devices or fasteners, such as staples, clips, tacks, sutures, and the like.

While current surgical implants and surgical methods perform satisfactorily, it would be advantageous to reduce the number of fasteners or tacking devices associated with device fixation.

SUMMARY

Medical devices are described herein in which a substrate is combined with a reactive component, wherein the combination of the substrate and the reactive component create a reactive implant capable of bonding with a tissue surface upon implantation. The reactive component may include genipin, isocyanates, N-hydroxy succinimides, cyanoacrylates, aldehydes, diimides, cyanamide, carbodiimides, dimethyl adipimidate, starches, and combinations thereof. In some embodiments, the reactive component is genipin. Additionally, the reactive component is present in the reactive implant in amount of from about 0.05% by weight of the reactive implant to about 5% by weight of the reactive implant.

Substrates or medical devices of the present disclosure used to create reactive implants may include a material such as gelatin, collagen, fibrin, fibrinogen, elastin, keratin, albumin, hydroxyethyl cellulose, cellulose, oxidized cellulose, hydroxypropyl cellulose, carboxyethyl cellulose, carboxymethyl cellulose, trimethylene carbonate, caprolactone, dioxanone, glycolic acid, lactic acid, glycolide, lactide, polytetrafluoroethylenes, polyethylene terephthalate, polyurethanes, and combinations thereof. Furthermore, the polymer substrate may be in the form of sutures, staples, stents, meshes, tapes, gauzes, soft tissue repair devices, buttresses, bands, ribbons, grafts, scaffolds, wound dressings, and foams. Additionally, the medical device may further possess a polymer coating or a bioactive agent.

In some embodiments, the reactive component contacts the substrate in situ. Alternatively, the reactive component is coated on at least a portion of a surface of the substrate. Yet in other embodiments, the substrate and the reactive component are contacted in situ. The reactive component may be in the form of a solution, the solution at a concentration of from about 0.1% w/v to about 10% w/v.

In another embodiment, the reactive implant includes a porous substrate in combination with a reactive component, wherein the reactive component crosslinks the porous substrate to at least one tissue surface. The reactive implant may include genipin.

A method for making the reactive implant is also disclosed, providing a substrate including collagen; contacting the substrate with a genipin solution creating a reactive implant; and, implanting the reactive implant in tissue. The method further includes monitoring bonding of the genipin with the tissue to determine the reaction rate of genipin with tissue. The method also may include monitoring the reaction by observing a color change in genipin to determine when the bonding of genipin with tissue is complete.

BRIEF DESCRIPTION OF THE DRAWINGS

The illustrative embodiments described herein will become more readily apparent from the following description, reference being made to the accompanying drawings in which.

DETAILED DESCRIPTION

Figure 1:
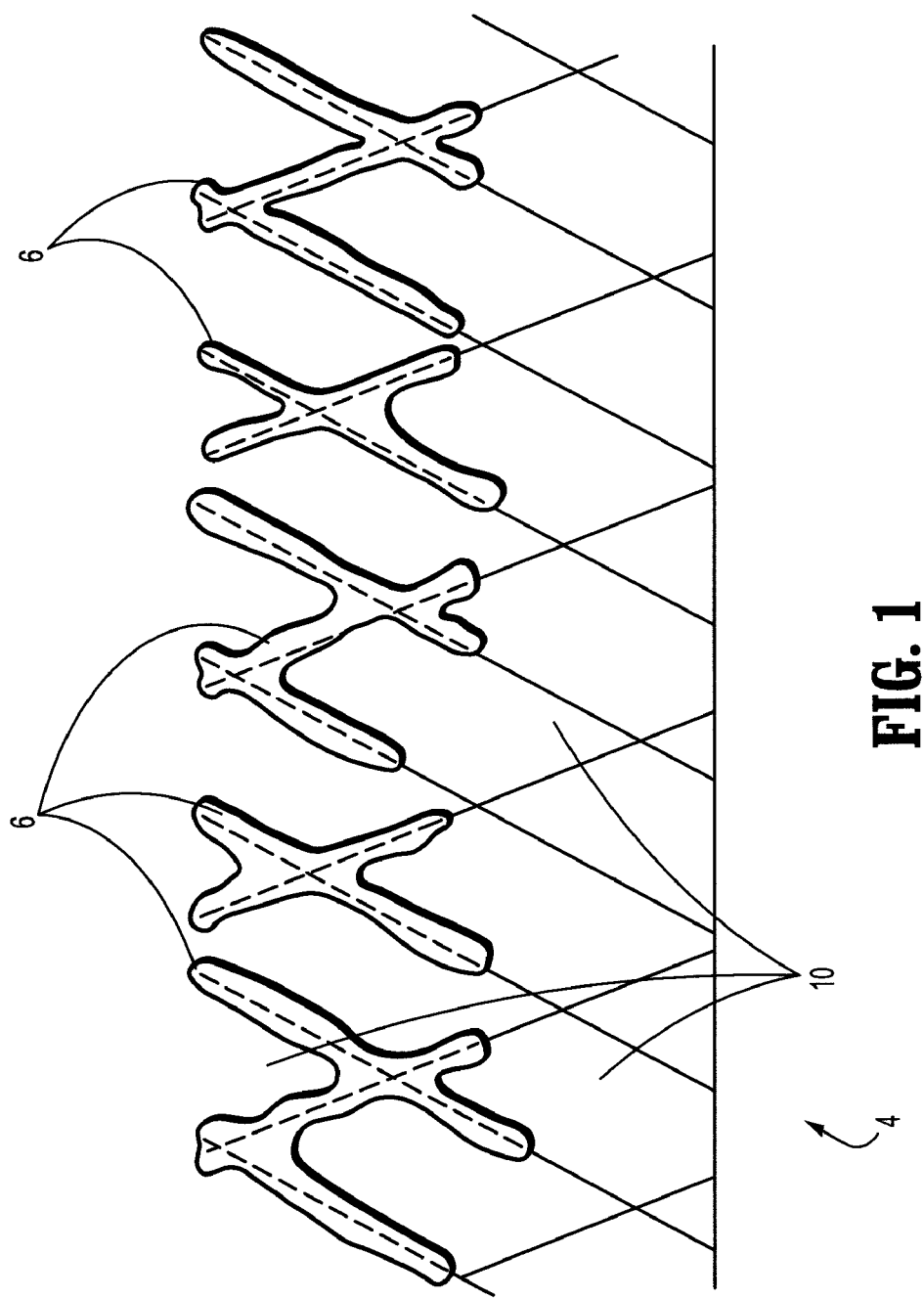
FIG. 1 shows a coated reactive implant in accordance with one embodiment of the present disclosure.

Medical devices described herein include a substrate used in combination with a reactive component creating a reactive implant. The reactive implant self-fixates to a tissue surface by crosslinking or chemically bonding with reactive groups present on the tissue surface. The term "chemical bonding" as used herein refers to all types of chemical bonding including covalent bonding, crosslinking, ionic bonding, and the like. Also as used herein, the term "device" and "implant" are interchangeable, however, once the device or implant contacts a reactive component, a "reactive device" or "reactive implant" is created. Also used herein, the term "reactive solution" includes a solution containing a reactive component.

Medical devices of the present disclosure can be made from biodegradable materials, non-biodegradable materials, and combinations thereof. Suitable synthetic biodegradable materials include polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly(ortho esters), hydroxy alkanoates, tyrosine carbonates, poly(imide carbonates), poly(imino carbonates) such as poly(bisphenol A-iminocarbonate) and poly(hydroquinone-iminocarbonate), polyurethanes, polyanhydrides, polymer drugs (e.g., polydiflunisol, polyaspirin, and protein therapeutics) and copolymers and combinations thereof.

Suitable natural biodegradable polymers include proteins such as collagen, gelatin, albumin, casein, poly(amino acids); polysaccharides such as cellulose, dextran, chitin, alginate, fucans, carboxymethyl cellulose and glycosaminoglycans; hyaluronic acid; gut; copolymers and combinations thereof.

More specifically, collagen as defined herein includes natural or derived collagen (including animal or bacterial recombinant) and collagen derivatives. Collagen implants may include collagen derived from human, animal, bacterial, or recombinant origin. Some non-limiting examples include type I porcine or bovine collagen, type I, II, III, or IV human collagen, or combinations thereof.

Collagen can be modified by using any method within the purview of those skilled in the art to provide pendant portions of the collagen with moieties which are capable of covalently bonding with the reactive chemical groups of a glycosaminoglycan. Examples of such pendant moieties include aldehydes, sulfones, vinylsulfones, isocyanates, and acid anhydrides. In addition, electrophilic groups such as —$CO_2N$ $(COCH_2)_2$, —$CO_2N(COCH_2)_2$, —$CO_2H$, —CHO, —$CHOCH_2$, —N=C=O, —$SO_2CH$=$CH_2$, —$N(COCH)_2$, —S—S—$(C_5H_4N)$ may also be added to pendant chains of the collagen to covalently bond to itself (i.e., the collagen) or allow covalent bonding to occur with the glycosaminoglycans.

In embodiments, the collagen may be modified through the addition of an oxidizing agent. Contacting collagen with an oxidizing agent creates oxidative cleavage along portions of the collagen thereby creating pendant aldehyde groups capable of reacting with the glycosaminoglycans. The oxidizing agent may be, for example, iodine, peroxide, periodic acid, hydrogen peroxide, a periodate, a compound containing periodate, sodium periodate, a diisocyanate compound, a halogen, a compound containing halogen, n-bromosuccinimide, a permanganate, a compound containing permanganate, ozone, a compound containing ozone, chromic acid, sulfuryl chloride, a sulfoxide, a selenoxide, an oxidizing enzyme (oxidase) and combinations thereof. In embodiments, the oxidizing agent may be periodic acid.

Non-biodegradable materials may also be used to construct medical devices of the present disclosure. Suitable materials include fluorinated polymers (e.g., fluoroethylenes, fluoropropylenes, fluoroPEGs); polyolefins such as polyethylene and ultra high molecular weight polyethylene (UHMWPE); polyesters such as polyethylene terepththalate (PET); nylons; polyamides; polyurethanes; silicones; polybutesters; polyethylene glycol; polyaryletherketone; copolymers and combinations thereof. Additionally, non-biodegradable polymers and monomers may be combined with each other and may also be combined with other various biodegradable polymers and monomers to create a reactive implant.

In certain embodiments, implants according to the present disclosure may be constructed at least in part using shape memory polymers. Suitable polymers used to prepare hard and soft segments of shape memory polymers include caprolactone, dioxanone, lactide, glycolide, polyacrylates, polyamides, polysiloxanes, polyurethanes, polyether amides, polyurethane/ureas, polyether esters, urethane/butadiene copolymers, and combinations thereof.

In some embodiments, the implant may include metals (e.g., steel or titanium), metal alloys including degradable alloys such as iron-based or magnesium-based degradable alloys, and the like.

In certain embodiments, implants include porous substrates. The term "porous" as used herein may define openings and spacings which are present as a surface characteristic or a bulk material property, partially or completely penetrating the medical device. Pores may be created using methods within the purview of those skilled in the art, including but not limited to processes such as sintering, leaching of salt, sugar or starch crystals, and knitting or weaving of fibers. For example, a mesh having openings defined by a weave or knit pattern may be considered a porous material. Alternatively, a foam scaffold may be considered a porous material. Porous materials may have an open-cell structure, where the pores are connected to each other, forming an interconnected network. Conversely, porous substrates may be closed cell foams where the pores are not interconnected.

In other alternate embodiments, meshes including composite meshes which have at least one substrate layer and one or more layers having a porous or non-porous construction may be used in forming a reactive implant. A non-porous layer may retard or prevent tissue ingrowth from surrounding tissues thereby acting as an adhesion barrier and preventing the formation of unwanted scar tissue. For example, a collagen composite mesh such as PARIETEX™ (Tyco Healthcare Group LP, dba Covidien) may be used in the reactive implant of the present disclosure. PARIETEX™ Composite mesh is a 3-dimensional polyester weave with a resorbable collagen film bonded on one side.

Other medical devices used to create reactive implants of the present disclosure include, but are not limited to, meshes, patches, scaffolds, soft tissue repair devices, sutures, staples, tacks, grafts, tapes, gauzes, buttresses, pledgets, tissue engineering scaffolds, stents and tissue wraps and combinations thereof.

A reactive component is combined with the medical device imparting reactive functional groups to the medical device surface, creating the reactive implant. Suitable reactive components may include crosslinkers, adhesives, sealants, couplers, and the like that are functionalized with at least one free reactive group capable of bonding the medical device to tissue. More specifically, reactive components include, but are not limited to, isocyanates, N-hydroxy succinimide ("NHS"), cyanoacrylates, aldehydes (e.g., formaldehydes, glutaraldehydes, glyceraldehydes, and dialdehydes), genipin, and other compounds possessing chemistries having some affinity for the substrate, tissue, or both. Reactive components of the present disclosure may also include any natural or synthetic crosslinker, including, but not limited to: aldehydes such as those listed above; diimides; diisocyanates; cyanamide; carbodiimides; dimethyl adipimidate; starches; and combinations thereof. The reactive components may be monofunctional, difunctional or multi-functional monomers, dimers, small molecules, or oligomers formed prior to or during implantation.

In one embodiment, the reactive component is genipin, as shown in Structure I.

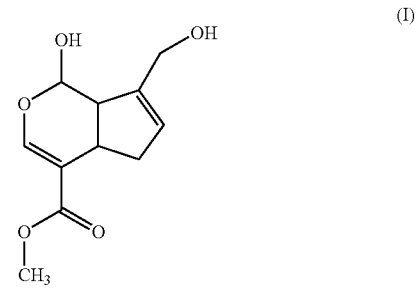

(I)

As used herein the term "genipin" includes, genipin, its derivatives, analogs, and any stereoisomer or mixture of stereoisomers of genipin. Genipin may be used as a natural crosslinker for amine-containing proteins including, but not limited to, collagen, elastin, gelatin, and chitosan. Genipin may be prepared by oxidation followed by reduction and hydrolysis or by enzymatic hydrolysis of the parent compound geniposide. Alternatively, racemic genipin may be prepared synthetically.

Genipin is colorless, but it reacts with primary free amines and subsequently undergoes oxidative polymerization, creating blue pigments. The blue pigments produced may provide an added benefit of a natural color identifier to visually locate the points of chemical attachment of the implant, such as a mesh. In other embodiments, the blue pigments formed during a chemical reaction may also be used to indicate to the user the degree of crosslinking. For example, an area with a darker blue color (when crosslinking with amines) may indicate that more crosslinking has occurred in that area, compared to a second area with lighter blue color (indicating less crosslink formation). Additionally, genipin may exhibit a specified degree of color change, associated with a specified degree of crosslinking.

Chemical Means of Attachment/Interaction

The substrate is combined with a reactive component having at least one free reactive group capable of chemically bonding with living tissue. In certain embodiments, the reactive component may crosslink with itself and around and/or throughout the substrate, while maintaining free reactive groups for crosslinking with a tissue surface. In other embodiments, the reactive component can crosslink with an amine-containing substrate or an amine-containing coating thereon and further react to tissue. In alternate embodiments, a first reactive group of the reactive component can be used to chemically bond to the substrate and a second reactive group of the reactive component can be used to chemically bond the substrate to tissue.

In some embodiments, the reactive component can be immobilized to the substrate by reacting with itself. For example, the reactive component can react with itself, encapsulating the substrate, forming an intricate network encompassing the substrate, or portions thereof. In other embodiments, when the substrate is porous, the reactive component may penetrate interstices or pores, reaching the interior of the implant. In certain embodiments, the reactive component may not chemically bond to the substrate (if no free amines are present). The reactive component may also maintain free reactive groups for further reacting with tissue.

In alternate embodiments, the reactive component can be immobilized to the substrate by chemical bonding with the substrate. Thus, the reactive component may have more than two reactive groups. For example, a first reactive group of the reactive component may react with the substrate and a second reactive group may remain free for reacting with tissue. More than one reactive group may be free for reacting with tissue; in embodiments from about 1 reactive group to about 8 reactive groups may be free for reacting with tissue. For example, the reactive component may be reactive to a proteinaceous implant. The chemical reaction between the reactive component and the implant may bind the reactive component to the implant while leaving some reactive groups unreacted for future chemical reactions with a tissue surface in situ.

Physical Means of Attachment/Interaction

The reactive component may be supplied as a coating on the medical device, termed herein a "reactive coating." FIG. 1 illustrates a mesh substrate 4, coated with a reactive coating 6. The mesh 4 includes pores 10 whereby the reactive coating does not fill the pores 10. However, it is envisioned that a reactive coating may wick into other porous substrates, penetrating and filling pores or interstices. The reactive coating 6 may reside on at least one side or at least a portion of the mesh 4 prior to sterilization and packaging. Methods for coating medical devices are within the purview of those skilled in the art, including but not limited to spraying, dipping, brushing, vapor deposition, co-extrusion, capillary wicking, film casting, molding and the like. The reactive component may be combined with the substrate in the form of a coating, film, foam, or powder on at least a portion of the substrate. The reactive component may be present in an amount of from about 0.001% by weight to about 10% by weight of the implant, in embodiments, from about 0.05% weight to about 5.0% weight of the reactive implant.

Alternatively, the reactive component may be immobilized to the substrate through mechanical interactions such as wicking into pores or capillary action. For example, with woven or knitted implants such as grafts or meshes, a genipin solution may be physically entrapped in pores or between fibers. It should be understood that other reactive solutions may also become physically entrapped in pores or between fibers. The implant may be further dried at a specified temperature and humidity level, removing residual solvent and leaving behind a reactive coating, creating a reactive implant.

Alternatively, the reactive coating may be applied to the device prior to implantation, for example soaking the medical device in a reactive solution in the operating room, prior to implantation.

For example, a reactive component may be supplied in a conduit to be used with a specialized injectable package material containing a substrate. Examples of an injectable package are disclosed in U.S. Patent Application Publication No. 2007/0170080 filed Jan. 26, 2006, the entire disclosure of which is incorporated by reference herein. The reactive component may be injected into the substrate package any time prior to surgical use. In embodiments, the reactive component, water soluble or dispersible, saturates and swells the substrate in preparation for use. A bioactive agent may also be added either to the reactive component or directly into the substrate package at the time of use.

Upon reacting with amine-containing tissues, the reactive implant should fixate to tissue within a useful time range. In alternate embodiments, the crosslinker may be chemically "shielded" or "blocked" in aid of slowing the reaction with tissue, or the crosslinker of interest may simply have slow reaction kinetics.

The amount of time necessary for the reactive component to bind the substrate to tissue may vary from about 1 second to about 6 hours, in embodiments about 30 seconds to about 2 hours.

Reactive components may be combined with solvents, including polar and non-polar solvents to create solutions or coatings which will be applied to medical devices of the present disclosure. Non-limiting examples of solvents include water; saline; buffer salts; alcohols including methanol, ethanol and propanol; dimethyl sulfoxide; dimethylformamide; chlorinated hydrocarbons (such as methylene chloride, chloroform, 1,2-dichloro-ethane); and aliphatic hydrocarbons such as hexane, heptene, ethyl acetate. Reactive components may be present in a solution from a concentration of about 0.1% w/v to about 10% w/v.

Figure 2:
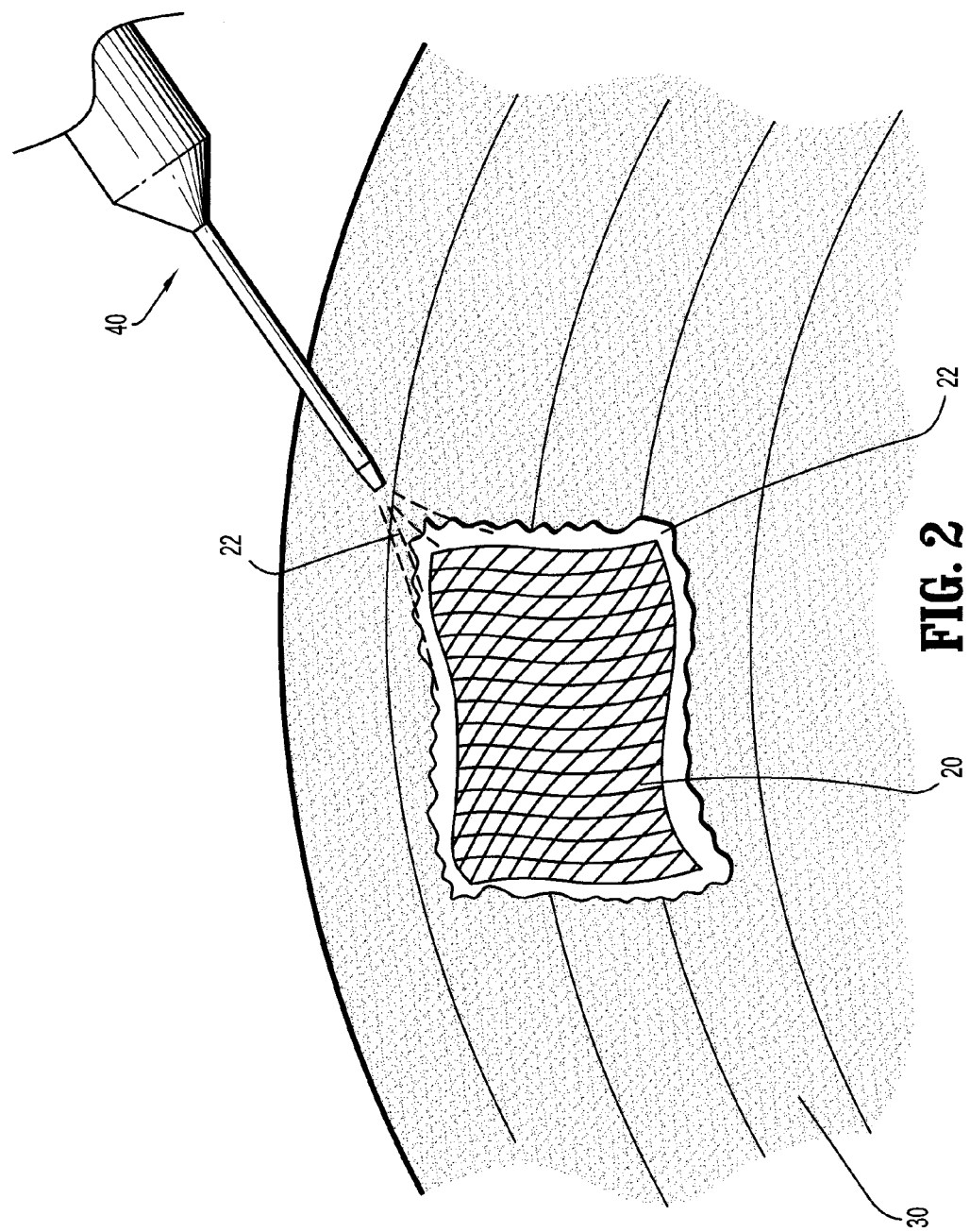
FIG. 2 shows an alternate embodiment of a reactive implant in accordance with the present disclosure.

FIG. 2 illustrates an alternate embodiment of a method by which the reactive implant may be created in situ. A reactive solution 22 is applied to an implant 20 in situ (creating a reactive implant), crosslinking the implant to a tissue surface 30. As shown, applicator 40 sprays the reactive solution 22 towards the implant 20, covering the implant 20. The reactive solution 22 crosslinks the implant 20 to the tissue surface 30, securing the implant 20 in situ. The reactive solution 22 covers the implant surface and may penetrate the mesh interstices (not shown). In certain embodiments, the reactive solution may be laparoscopically sprayed into the body. The reactive substrate may react with functional groups in tissue such as primary amine groups, secondary amine groups, hydroxyl groups, carboxylic groups, sulfonic groups and combinations thereof, and the like.

In certain embodiments, reactive implants of the present disclosure may further include a coating. Coatings may be applied to the implant for various reasons including increasing lubricity (for insertion), altering the chemical reactivity of the implant surface, promoting or preventing adhesions, or increasing biocompatibility. Coatings for implants may include any of the absorbable and non-absorbable materials listed above. In embodiments, the coating may include a polymer such as collagen. Coatings may be applied to implants using any method within the purview of those skilled in the art including, but not limited to, dip coating, spray coating, solvent evaporation and the like.

In some embodiments, at least one bioactive agent may be combined with the substrate or reactive component utilized to form an implant of the present disclosure, or both. The term "bioactive agent", as used herein, is used in its broadest sense and includes any substance or mixture of substances that have clinical use. A bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the medical device in any suitable form of matter, e.g., films, powders, liquids, gels, combinations thereof, and the like.

Non-limiting examples of classes of bioactive agents which may be utilized in accordance with the present disclosure include anti-adhesives, antimicrobials, anti-infectives, anti-thrombotics, analgesics, antipyretics, anesthetics, antiepileptics, antihistamines, anti-inflammatories, anti-proliferatives, cardiovascular drugs, diagnostic agents, chemo agents, telomerase inhibitors, polymer drugs including polyaspirin and polydiflunisal, anti-platelet drugs, platelet activating drugs, angiogenic agents, gene therapy agents, protein therapeutics, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the implantable medical device and the surrounding tissues. In addition, anti-adhesive agents may be used to prevent adhesions from forming between the coated implantable medical device and the packaging material. Some examples of these agents include, but are not limited to, poly(vinyl pyrrolidone), carboxymethyl cellulose, hyaluronic acid, alginate, collagen, polyethylene glycol, polyethylene oxide, poly vinyl alcohols and combinations thereof. As noted above, in embodiments the materials utilized to form the substrate may include these materials, and thus an implant including such a substrate may function as an anti-adhesion barrier without the inclusion of any additional bioactive agents.

Suitable antimicrobial agents which may be included as a bioactive agent of the present disclosure include triclosan, also known as 2,4,4'-trichloro-2'-hydroxydiphenyl ether; chlorhexidine and its salts, including chlorhexidine acetate, chlorhexidine gluconate, chlorhexidine hydrochloride, and chlorhexidine sulfate; silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin, tetracycline; aminoglycosides, such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil; nonoxynol 9; fusidic acid; cephalosporins; and combinations thereof. In addition, antimicrobial proteins and peptides such as lactoferrin and lactoferricin B and antimicrobial polysaccharides such as fucans and derivatives thereof may be included as a bioactive agent in the present disclosure.

Other bioactive agents which may be included as a bioactive agent in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as vasodilators and nitroglycerin; alkaloids; analgesics; narcotics such as codeine, dihydrocodeinone, meperidine, and morphine; non-narcotics such as salicylates, aspirin, acetaminophen, and d-propoxyphene; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; polymer drugs (e.g., polydiflunisol, polyaspirin, and protein therapeutics); prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents include viruses and cells; peptides; polypeptides and proteins, analogs, muteins, and active fragments thereof, such as immunoglobulins, antibodies, nanobodies, cytokines (e.g., lymphokines, monokines, chemokines); blood clotting factors; hemopoietic factors; interleukins (IL-2, IL-3, IL-4, IL-6), interferons (3-IFN, a-IFN and y-IFN); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists and protein agonists; nucleic acids, such as antisense molecules, DNA, DNA intercalators, RNA, RNAi, oligonucleotides, polynucleotides, and ribozymes.

The following examples are being submitted to illustrate embodiments of the present disclosure. These examples are intended to be illustrative only and are not intended to limit the scope of the present disclosure. Also, parts and percentages are by weight unless otherwise indicated.

EXAMPLES

The following non-limiting examples show possible surgical implants such as meshes, packaging considerations for combining the substrate and the reactive component for controlling the reaction kinetics, and optional bioactive agents that may be added to the substrate to impart additional characteristics to the implant.

Example 1

A solution including polyethylene glycol end-capped with an NHS ester in methylene chloride is prepared at a concentration of about 40% w/v. A PARIETEX™ mesh from Covidien, is dip coated in the solution and dried in an oven overnight at ambient temperature, removing any remaining solvent. The mesh is then implanted in situ, and the reactive implant (mesh) will, in the presence of tissue having a presenting amine, crosslink the collagen mesh to tissue, thereby forming an interpenetrating network. The reaction may take up to 30 minutes to complete.

Example 2

A reactive component is supplied in a conduit to be used in concert with a specialized injectable package containing a graft substrate. The reactive component may be injected into the graft package immediately prior to surgical use. The reactive component, water soluble or dispersible, saturates and swells the graft substrate in preparation for use.

Upon removal from the provided package, the implant is designed to react within a specified time range. Optionally, the crosslinker may be chemically shielded or blocked by a water soluble coating or a coating including buffer salts to slow the reaction, enabling the surgeon to reposition the graft if required.

Example 3

A polyester mesh is provided and properly positioned in situ by a surgeon. Once positioned, a genipin solution at a concentration of about 60 mg/mL is laparoscopically sprayed in situ, covering the mesh. The genipin solution covers the mesh and the surrounding tissue, creating a reactive implant. Over the next few hours, the genipin solution crosslinks the mesh to tissue, fixating the mesh in place.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A medical device comprising:
a substrate in combination with a reactive component having at least one free reactive group, wherein the combination of the substrate and the reactive component create a reactive implant for chemically bonding the reactive implant with a tissue surface upon implantation, wherein the reactive component is present on the reactive implant in an amount of from about 0.05% by weight of the reactive implant to about 5% by weight of the reactive implant and wherein the reactive component is genipin.

2. The medical device of claim 1, wherein the substrate comprises a material selected from the group consisting of gelatin, collagen, fibrin, fibrinogen, elastin, keratin, albumin, hydroxyethyl cellulose, cellulose, oxidized cellulose, hydroxypropyl cellulose, carboxyethyl cellulose, carboxymethyl cellulose, trimethylene carbonate, caprolactone, dioxanone, glycolic acid, lactic acid, glycolide, lactide, polytetrafluoroethylenes, polyethylene terephthalate, polyurethanes, and combinations thereof.

3. The medical device of claim 1, wherein the reactive component contacts the substrate in situ.

4. The medical device of claim 1, wherein the reactive component is coated on at least a portion of a surface of the substrate.

5. The medical device of claim 1, wherein the substrate and the reactive component are contacted in situ.

6. The medical device of claim 1, wherein the reactive component comprises a solution at a concentration of from about 0.1% w/v to about 10% w/v.

7. The medical device of claim 1, wherein the substrate is selected from the group consisting of sutures, staples, stents, meshes, tapes, gauzes, soft tissue repair devices, buttresses, bands, ribbons, grafts, scaffolds, wound dressings, and foams.

8. The medical device of claim 7, wherein the medical device is a mesh.

9. The medical device of claim 1, wherein the medical device further comprises a polymer coating.

10. The medical device of claim 1, wherein the medical device further comprises a bioactive agent.

11. A reactive implant comprising a porous substrate in combination with a reactive component, wherein the reactive component includes a first reactive group that chemically bonds the reactive component to the porous substrate and a second reactive group that crosslinks the porous substrate to at least one tissue surface, wherein the reactive component is present on the reactive implant in an amount of from about 0.001% by weight of the reactive implant to about 10% by weight of the reactive implant, and wherein the reactive component is genipin.

* * * * *